United States Patent [19]

Markussen

[11] Patent Number: 4,489,159

[45] Date of Patent: Dec. 18, 1984

[54] PROCESS FOR PREPARING ESTERS OF HUMAN INSULIN

[75] Inventor: Jan Markussen, Herlev, Denmark

[73] Assignee: Novo Industri A/S, Denmark

[21] Appl. No.: 406,571

[22] Filed: Aug. 9, 1982

[30] Foreign Application Priority Data

Aug. 10, 1981 [DK] Denmark .............................. 3537/81

[51] Int. Cl.³ .......................... C12P 21/04; C12N 9/76
[52] U.S. Cl. ........................................ 435/71; 435/213
[58] Field of Search ...................... 435/71, 70, 68, 69, 435/213

[56] References Cited

U.S. PATENT DOCUMENTS

| 3,276,961 | 10/1966 | Bodanszky et al. | 424/178 |
|---|---|---|---|
| 3,903,068 | 9/1975 | Ruttenberg | 260/112.7 |
| 4,320,196 | 3/1982 | Morihara et al. | 435/70 |
| 4,320,197 | 3/1982 | Morihara et al. | 435/70 |
| 4,343,898 | 8/1982 | Markussen | 435/70 |

OTHER PUBLICATIONS

Butler et al., Arch. Biochem. Biophys., 178, 43–50 (1977).
Morihara et al., Nature, 280, 412–413 (1979).
Obermeier et al., Hoppe-Seyler's Z. Physiol. Chem. 357, 759–767 (1976).
Schmitt et al., Hoppe-Seylers Z. Physiol. Chem., 359, 799–802 (1978).

Primary Examiner—Esther M. Kepplinger
Attorney, Agent, or Firm—Fidelman, Wolffe & Waldron

[57] ABSTRACT

A process for converting human des-B30-insulin, namely

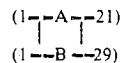

I into h-In-Thr$^{B30}$ esters through amidation with an L-threonine ester in a mixture of water and a water miscible solvent in the presence of trypsin and optionally an acid.

Yields in excess of at least 90% are obtained by limiting water content to 10%–30% v/v of the reaction mixture.

12 Claims, No Drawings

PROCESS FOR PREPARING ESTERS OF HUMAN INSULIN

This invention relates to conversion of des-B30 porcine insulin into human insulin via a threonine B30 derivative of human insulin. U.S. Pat. No. 4,343,898 copending herewith as patent application, Ser. No. 233,051, filed Feb. 10, 1981, is a related application.

BACKGROUND OF THE INVENTION

In the treatment of diabetes mellitus insulin preparations derived from porcine or bovine insulin have generally been used. Bovine, porcine, and human insulins exhibit minor differences with respect to their amino acid sequence, the difference between human and porcine insulin being confined to a single amino acid in that the B30 amino acid of human insulin is threonine, whereas that of porcine insulin is alanine. However, it could be argued that the ideal insulin preparation for human beings would be an insulin having exactly the same chemical structure as that of human insulin.

For the production of natural human insulin the necessary amount of human pancreas glands is not available.

Synthetic human insulin has been prepared on a small scale at great expense, vide Helv. Chim. Acta 57, 2617, and 60, 27.

Semi-synthetic human insulin has been prepared from porcine insulin by what are believed to be a tedious pathway, vide Hoppe-Seyler's Z. Physiol. Chem. 357, 759.

One known semi-synthetic process for preparing human insulin comprises the following three steps: First, porcine insulin is converted into porcine des-(Ala$^{B30}$)-insulin by treatment with carboxypeptidase A, vide Hoppe-Seyler's Z. Physiol. Chem. 359, 799. In the second step, porcine des-(Ala$^{B30}$)-insulin is subjected to a trypsin-catalyzed coupling with Thr-OBu$^t$, whereby human insulin Thr$^{B30}$-tert-butyl ester is formed. Finally, said ester is treated with trifluoroacetic acid yielding human insulin, vide Nature 280, 412. The first step, however, results in a partial removal of Asn$^{A21}$, yielding des-(Ala$^{B30}$, Asn$^{A21}$)-insulin. This derivative gives, after the two subsequent reactions, rise to a contamination by des-(Asn$^{A21}$)-insulin in the semi-synthetic human insulin product, a contamination which cannot easily be removed with known preparative methods. Des-(Asn$^{A21}$)-insulin possesses low biological activity (about 5%), vide Amer. J. Med. 40, 750.

Direct conversion of porcine insulin into human insulin by traspeptidation was suggested in U.S. Pat. No. 3,276,961, but the process suggested employs conditions under which splitting of the Arg$^{B22}$-Gly$^{B23}$ takes place, vide J. Biol. Chem. 236, 743.

Related U.S. patent application, Ser. No. 233,051 filed Feb. 10, 1981, now U.S. Pat. No. 4,343,898 relates to a transpeptidation process for preparing semi-synthetic human insulin from porcine insulin via a threonine B30 derivative. High yields are obtained by the process of this related patent, and in all respects, the patent process is believed to be well adapted to conversion of porcine insulin into human insulin.

The present invention relates to an alternative process which might be competitive with the process of related U.S. Pat. No. 4,343,898. Surprisingly, it has been found that the reaction conditions and reactants suited to the transpeptidation of porcine insulin are applicable to amidation of porcine des-(Ala$^{B30}$)-insulin into the threonine$^{B30}$ esters of human insulin. Specifically, the method herein described results in yields of threonine$^{B30}$ esters of human insulin exceeding 90%.

A like amidation process for preparing human insulin from porcine des-(Ala$^{B30}$)-insulin has been described in European patent application No. 80,101,966, vide also Nature 280 (1979), 412, and U.S. Pat. Nos. 4,320,196 and 4,320,197. According to the U.S. patents the amidation is preferably performed in a medium containing 0 to 65%, preferably 40 to 60%, of an organic solvent. Furthermore, the preferred reaction temperature is between 20° C. and 40° C., the temperature 37° C. being used in the examples. The yield of coupling was by HPLC (high pressure liquid chromatography) from 50–80%. According to the Nature paper, the yield was 73%.

An amidation process for preparing human insulin from porcine des-(Ala$^{B30}$)-insulin has been described also in Proceedings of the 2nd International Insulin Symposium, Aachen, Federal Republic of Germany, 1979. According to said paper, the amidation was performed in a medium containing about 60% of organic solvent and the reaction was performed at 38° C. The yield of coupling was determined by HPLC to be 67%.

An amidation process for preparing human insulin from porcine des-(Ala$^{B30}$)-insulin has been described also in Proceedings of the 16th European Peptide Symposium, Helsingør, Denmark, 1980. According to said paper, the process was performed in a medium containing about 60% organic solvent. Probably, the reaction temperature was 37° C. After a reaction time of 30 minutes, the yield was 85%, however, the yield was decreased to 70% after 22 hours.

One of the reasons for the low yields by the amidation processes known heretofore is the loss of insulin due to undesired side reactions, e.g., forming DOI-Thr($R^2$)-$R^1$, wherein DOI represents porcine des-octapeptide-(B23-B30)-insulin; $R^1$ and $R^2$ represent whatever carboxy and hydroxyl protecting group is present on the threonine moiety.

The objective of the present invention was to discover process conditions under which the yield of reaction product is extremely high, specifically, is higher than 90%.

Surprisingly, yields exceeding 90% are obtainable by the use of a much lower concentration of water in the reaction mixture than by the known amidation processes.

Preferably, the amidation is carried out at lower temperatures such as at below room temperature, i.e., at 25° C. or less.

The object of this invention is to provide a process for converting human des-B30-insulin into a threonine B30 ester of human insulin in yields exceeding 90%.

BRIEF STATEMENT OF THE INVENTION

The process according to this invention comprises reacting the human des-B30-insulin or a salt or complex thereof with an excess of an L-threonine ester or a salt thereof in a mixture of water and a water miscible organic solvent in the presence of trypsin wherein the content of water in the reaction mixture is between 10% and 30%.

The reaction temperature range is from the freezing point of the reaction mixture to 37° C. The preferred range is above 0° C. The reaction may require several days.

Optionally present in the reaction mixture is an acid, preferably an organic acid, in up to 10 equivalents per equivalent of the threonine ester.

Thus, the process, according to the present invention, can be performed by dissolving human des-B30-insulin, and L-threonine ester and trypsin in a mixture of water and at least one water miscible organic solvent, optionally in the presence of an acid then holding at a temperature in the 0°–37° C. temperature range for 1–96 hours.

DISCUSSION OF THE INVENTION

Although des-B30-insulin from any source of the insulin may be amidated by practice of this invention, formation of human insulin as is desired herein requires that the original source of the des-B30-insulin contain the human insulin moiety:

Porcine insulin, for differing from human insulin only by containing Ala at B30 instead of Thr at B30 is a convenient and preferred source of human des-B30-insulin. The porcine source des-B30-insulin, termed appropriately porcine des-(Ala$^{B30}$)-insulin, may be obtained as described in Example (1) in U.S. Pat. Nos. 4,320,196 or 4,320,197, or elsewhere in the prior art.

As has already been pointed out the amidation process of this invention is carried out in solution in a mixture of water and one or more water miscible organic solvents, and optionally, but preferably an acid.

The water content is held to 10–30% v/v of the reaction mixture.

The optimum water content depends on which water miscible organic solvent is used, on the chosen reaction temperature and on the presence or absence of an acid in the reaction mixture. The content of water in the reaction mixture should always not exceed about 30% (v/v), preferably be less than about 25% (v/v), and more than about 10% (v/v), and preferably be more than about 15% (v/v). The preferred range then is 15%–25% v/v water.

One advantage of decreasing the amount of water in the reaction mixture from levels employed heretofore is that thereby the formation of by-products is decreased. Similarly, by including the acid in the reaction mixture it is possible to decrease the formation of by-products. The increase in yield obtained by practice of this invention is positively correlated to a low content of water in the reaction mixture. In order to prevent denaturation of the enzyme in reaction mixtures with a low content of water, the reaction temperature should preferably be substantially lower than reaction temperatures traditionally used in peptide synthesis with trypsin, viz. lower than about 37° C. As has already been pointed out, the preferred reaction temperature range is 0° C.–25° C.

The organic solvents suited to practice of this invention are polar solvents which are miscible with water and preferably such that are capable of containing therein high concentrations of insulin compounds and threonine ester. Examples of such suitable organic solvents are aprotic solvents, such as N,N-dimethylformamide, N,N-dimethylacetamide, N-methylpyrrolidone, hexamethylphosphortriamide, dioxane, acetone, tetrahydrofuran, formamide; acetonitrile, and dimethylsulfoxide (DMSO), and protic solvents, such as ethanol, methanol, 2-propanol, and 1,2-ethanediol. The nature of the solvent does effect the system as a whole, and interrelationships suited to one solvent productive of high amidation yields may not apply with a different solvent. Best yield results have been obtained with aprotic solvents, and aprotic solvents are most preferred for practice of this invention.

The addition of an acid, such as hydrochloric, formic, acetic, propionic, or butyric acid, or of a base, such as pyridine, TRIS, N-methylmorpholine, or N-ethylmorpholine, is optional. This invention may be practiced without addition of acid or base. They are included in the reaction mixture to bring about a suitable buffer system. Although mineral acids or bases may be used in practice of this invention organic acids and bases are preferred, particularly those identified above. The acid content may range from zero to 10 equivalents per equivalent of threonine ester, and preferably 0.5–5 equivalents acid per equivalent of the ester. The threonine ester may be added to the reaction mixture as the free base. Better yields are obtained when an acid is added to the reaction mixture, the amount of acid needed for obtaining optimal yields being dependent on the choice of organic solvent. For example, with an aprotic solvent like N,N-dimethylacetamide highest yields have been obtained with about three mols of acetic acid per mol of threonine ester.

The trypsin type is not material to practice of this invention. Trypsin is a well characterized enzyme available in high purity, notably from bovine, porcine and some microbial origin. Moreover, the trypsin form, whether it is native trypsin or an active immobilized trypsin or trypsin derivative is not material to practice of this invention. The term trypsin as employed herein is intended to include trypsins from all sources and all forms of trypsin that retain the amidation activity herein employed including proteases with trypsin-like specificity, e.g., Achromobacter lyticus protease. Ions which stabilize trypsin, e.g., calcium ions, may be present in the reaction mixture.

As examples of active trypsin derivatives can be mentioned acetylated trypsin, succinylated trypsin, glutaraldehyde treated trypsin, and immobilized trypsin derivatives.

If an immobilized trypsin is used it is suspended in the reaction medium.

To a great extent the action of trypsin is controlled by an interrelation of water and solvent content, and the acid/base ratio, which together favor the amidation action and suppress undesired trypsin catalyzed side reactions. Increasing the concentration of organic solvent in the reaction mixture from levels employed heretofore conduces to both, but also increases the rate at which irreversible trypsin denaturation occurs. However, the latter may be at least partly counteracted by decreasing the reaction temperature below 37° C. Reducing temperature also reduces the amidation rate, but such reduction may be compensated for by increasing reaction time. Since the denaturation rate is reduced more than the amidation rate, conduct of the present process at below room temperature is advantageous. Temperatures above 0° C., i.e., 0° C.–25° C. are preferred. Overall, reaction times of 1–96 hours are contemplated for practice of this invention.

The weight ratio between trypsin (calculated as crystalline trypsin or an amount of trypsin derivative corresponding thereto) and the human des-B30-insulin in the reaction mixture is normally in the range of from 1:200 to 1:1, preferably above 1:50.

Inasmuch as high concentrations of the des-B30-insulin and of threonine ester in solution promote high conversion rates, solvent selection is biased towards those solvents in which the reactants are very soluble. The solubility of the threonine ester in particular is important, because that reactant should be present in high concentration. The molar ratio of threonine ester to the des-B30-insulin should preferably exceed 5:1, the threonine ester concentration in the reaction mixture preferably being at least 0.1 molar.

The L-threonine esters contemplated for practice of this invention can be depicted by the following formula:

$$\text{Thr}(R^5)\text{—}OR^4 \qquad \text{II}$$

wherein $R^4$ represents a carboxyl protecting group, and $R^5$ represents hydrogen or a hydroxyl protecting group. Presence of a protecting group on the hydroxyl is optional.

Applicable threonine esters of the above formula are such, in which $R^4$ is a carboxyl protecting group which can be removed from the human insulin ester under conditions which do not cause substantial irreversible alterations in the insulin molecule. As examples of such carboxyl protecting groups can be mentioned lower alkyl, notably, methyl, ethyl, and tert-butyl, substituted benzyl groups such as p-methoxybenzyl, diphenylmethyl, and 2,4,6-trimethylbenzyl, and groups of the general formula:

$$-CH_2-CH_2-SO_2R^6,$$

wherein $R^6$ represents lower alkyl, such as methyl, ethyl, propyl, and n-butyl.

Suitable hydroxyl protecting groups $R^5$ are those which can be removed from the threonine B30 derivative of human insulin under conditions which do not cause substantial irreversible alteration in the insulin molecule. As an example of such a group can be mentioned tert-butyl.

Further protection groups usually used are described by Wünch: Metoden der Organischen Chemie (Houben-Weyl), Vol. XV/1, editor: Eugen Müller, Georg Thieme Verlag, Stuttgart 1974.

Lower alkyl groups contain less than 7 carbon atoms, preferably less than 5 carbon atoms.

Some of the threonine ester compounds of the above formula are known compounds and the remaining compounds of the above formula can be prepared in analogy with the preparation of known compounds or in analogy with known methods.

The threonine esters of the above formula may be employed in the form of the free bases or suitable salts thereof such as hydrochlorides, acetates, propionates, and butyrates.

Examples of a complex or salt of human des-B30-insulin is a zinc complex or zinc salt.

The amidation carried out by practice of this invention, will, therefore, result in compounds of the formula:

$$(\text{Thr}(R^5)\text{—}OR^4)^{B30}\text{—}h\text{-In} \qquad \text{III}$$

wherein —h-In designates human des-(Thr$^{B30}$)-insulinyl, and $R^4$ and $R^5$ are as defined above.

Human insulin can be obtained from the above human insulin esters of the formula III by removal of the protecting group $R^4$ and any protecting group $R^5$ by known methods or methods known per se. In case $R^4$ is methyl, ethyl, or a group:

$$-CH_2-CH_2-SO_2R^6,$$

wherein $R^6$ is as defined above, the said protecting group can be removed at gentle basic conditions in an aqueous medium, preferably at a pH value of about 8–12, e.g., at about 9.5. For the base can be used ammonia, triethylamine, bicarbonate/carbonate buffers or hydroxides of alkali metals such as sodium hydroxide. In case $R^4$ is tert-butyl, substituted benzyl such as p-methoxybenzyl or 2,4,6-trimethylbenzyl, or diphenylmethyl, the said group can be removed by acidolysis, preferably with trifluoracetic acid. The trifluoroacetic acid may be non-aqueous or may contain some water, or it may be diluted with an organic solvent, such as dichloromethane. In case $R^5$ is tert-butyl said group can be removed by acidolysis, vide above.

Preferred threonine reactants and then the threonine$^{B30}$ derivatives of the formulae II and III, respectively, are compounds wherein $R^5$ is hydrogen.

A process for preparing porcine des-(Ala$^{B30}$)-insulin is described in Hoppe-Seyler's Z. Physiol. Chem. 359 (1978), 799 et seq.

Selecting the reaction conditions according to the above explanation, taking into consideration the reaction conditions in the following examples, makes possible conduct of amidation with a yield of the threonine$^{B30}$ derivative of human insulin (Formula III) which is higher than 90% and even higher than 95%.

A preferred procedure for preparing human insulin from a threonine$^{B30}$ derivative of human insulin is as follows:

(1) If there is any trypsin activity left after the amidation, it is preferable to remove it under conditions where trypsin is inactive, for example, in acid medium below a pH-value of 3. Trypsin can be removed by separation according to molecular weight, for example, by gel-filtration on a "Sephadex G-50" gel or on a "Bio-Gel P-30" gel in acetic acid, vide Nature 280 loc. cit.

(2) Impurities such as unreacted des-(B30-)-insulin may be removed by the use of anion and/or cation exchange chromatography.

(3) Thereafter, the threonine$^{B30}$ ester of human insulin is deblocked and human insulin is isolated, e.g., crystallized, in a manner known per se.

By this process, human insulin of an acceptable pharmaceutical purity can be obtained and be further purified if desired.

Abbreviations used are in accordance with the rules approved (1974) by the IUPAC-IUB Commission on Biochemical Nomenclature, vide Collected Tentative Rules & Recommendations of the Commission on Biochemical Nomenclature IUPAC-IUB, 2nd ed., Maryland 1975.

For further understanding of this invention there follows numerous Examples. For a description of the analytic procedures used to ascertain the results provided in the Examples, reference is made to the aforementioned U.S. Pat. No. 4,343,898. The Examples wherein more than 90% yield is obrtained illustrate preferred embodiments of the process of this invention.

EXAMPLE 1

10 mg of porcine des(Ala$^{B30}$)-insulin was dissolved in 100 μl of 10 M acetic acid. To 50 μl of this solution were added: 100 μl of 2 M Thr-OMe (Me designates methyl) in N,N-dimethylacetamide, 60 μl of N,N-dimethylacetamide, 15 μl of water and 10 μl of a solution of trypsin (8% weight/volume) in 0.05 M calcium chloride. After incubation at 4° C. for 24 hours the product was precipitated with 8 ml of acetone, isolated by centrifugation, washed with 8 ml of acetone, isolated by centrifugation and dried in vacuo. The yield of (Thr-OMe)$^{B30}$-h-In was determined by HPLC. The product was dissolved in 2 ml of 1 M acetic acid and 100 μl of the solution was applied to a 4×200 mm "Nucleosil 5 C$_{18}$ column" for reverse-phase HPLC, using a 0.2 M ammonium sulphate buffer adjusted to a pH-value of 3.5 and containing 26.8% (volume/volume) acetonitril as the eluent. At a flow rate of 1 ml/min., des(Ala$^{B30}$)-insulin eluted after 18 minutes and (Thr-OMe)$^{B30}$-h-In after 24 minutes. The by-product of the reaction, viz. (Thr-OMe)$^{B23}$-des-heptapeptide-(B24-B30)-insulin eluted at 7 minutes. The detection and quantitation of the proteins was based on the extinction at 280 nm. The analysis gave the following distribution of compounds:

(Thr-OMe)$^{B30}$-h-In: 97.1%
des(Ala$^{B30}$)-insulin: 2.5%
(Thr-OMe)$^{B23}$-des-heptapeptide(B24-B30)-insulin: 0.4%

EXAMPLES 2 to 16

The following Examples 2 to 16 in Table 1 were carried out analogically to Example 1, changing the parameters of the reaction as shown in said table. However, in all examples 10 μl of 8% trypsin in an aqueous solution, 100 μl of organic solvent containing a threonine derivative of formula II and 50 μl of acetic acid containing 20% des(Ala$^{B30}$)-insulin was added. The molarity of the threonine derivative of formula II in said organic solvent and of said acetic acid appears from Table 1. The reaction time was 24 hours. In Table 1 the following abbreviations have been used:

HOAc is acetic acid, DMAA is N,N-dimethylacetamide, DMF is N,N-dimethylformamide, DMSO is dimethylsulfoxide, NMP is N-methylpyrrolidone and THF is tetrahydrofuran.

In case (Thr-OBu$^t$)$^{B30}$-h-In and (Thr(Bu$^t$)-OBu$^t$)$^{B30}$-h-In were synthesized, vide Example 15 and 16, the elution by HPLC was accomplished by applying a gradient in acetonitril from 26.8% to 40% (v/v).

EXAMPLES 17 to 34

These examples were performed in analogy with Examples 1 to 16 with the proviso that the reaction time was 4 hours. In each of these examples the yield was the same as those obtained in Examples 1 to 16, respectively.

It appears from a comparison of Examples 1 to 16 with Examples 17 to 34, respectively, that the same yields were obtained and this, inter alia, differentiates the novel process described in said examples from the known process described in Proceedings of the 16th European Peptide Symposium, supra. Hence, the time dependency has been eliminated.

EXAMPLE 35

250 mg of crystalline (Thr-OMe)$^{B30}$-h-In was dispersed in 25 ml of water and dissolved by the addition of 1 N sodium hydroxide solution to a pH-value of 10.0. The pH value was kept constant at 10.0 for 24 hours at 25° C. The human insulin formed was crystallized by the addition of 2 g of sodium chloride, 350 mg of sodium acetate trihydrate and 2.5 mg of zinc acetate dihydrate followed by the addition of 1 N hydrochloric acid to obtain a pH-value of 5.52. After storage for 24 hours at 4° C. the rhombohedral crystals were isolated by centrifugation, washed with 3 ml of water, isolated by centrifugation, and dried in vacuo. Yield: 220 mg of human insulin.

I claim:

1. In a process for preparing human insulin by amidating human des-B30 insulin or salt or complex thereof with an L-threonine ester or a salt thereof in the presence of trypsin followed by subjecting the resulting human insulin Thr$^{B30}$-ester to one or more reactions to remove all protecting groups, the improvement which comprises:

amidating in a mixture of water and a water miscible solvent with a water content in such reaction mixture exceeding about 10% and being less than 30% v/v, at a reaction temperature below about 37° C. to human insulin Thr$^{B30}$-ester in at least 90% yield.

2. The process, according to claim 1, further comprising presence of up to ten equivalents of acid per equivalent of the L-threonine ester in the reaction mixture.

3. The process, according to claim 2, characterized in that the concentration of L-threonine ester in the reaction mixture exceeds 0.1 molar.

| Example No. | organic solvent | molarity of threonine derivative M | molarity of HOAc M | further addition of organic solvent, μl | H$_2$O μl | temp. °C. | yield % | R$^4$ | R$^5$ | Estimated approximated concentration of water in reaction mixture (%) |
|---|---|---|---|---|---|---|---|---|---|---|
| 2 | DMAA | 2 | 10 | 60 | 15 | 12 | 97 | Me | H | 20 |
| 3 | DMAA | 2 | 10 | 60 | 15 | 25 | 97 | Me | H | 20 |
| 4 | DMAA | 2 | 10 | 75 | 0 | 4 | 93 | Me | H | 13 |
| 5 | DMF | 2 | 10 | 60 | 15 | 4 | 97 | Me | H | 20 |
| 6 | DMF | 2 | 10 | 60 | 15 | 12 | 97 | Me | H | 20 |
| 7 | DMF | 2 | 10 | 60 | 15 | 25 | 97 | Me | H | 20 |
| 8 | DMSO | 2 | 10 | 60 | 15 | 4 | 97 | Me | H | 20 |
| 9 | DMSO | 2 | 10 | 60 | 15 | 12 | 94 | Me | H | 20 |
| 10 | NMP | 2 | 10 | 60 | 15 | 4 | 96 | Me | H | 20 |
| 11 | NMP | 2 | 10 | 60 | 15 | 12 | 97 | Me | H | 20 |
| 12 | DMAA | 2 | 4 | 60 | 15 | 12 | 88 | Me | H | 27 |
| 13 | DMAA | 2 | 4 | 75 | 0 | 12 | 94 | Me | H | 21 |
| 14 | DMF | 2 | 4 | 60 | 15 | −22 | 90 | Me | H | 27 |
| 15 | DMAA | 2 | 10 | 60 | 15 | 12 | 97 | Bu$^t$ | H | 20 |
| 16 | DMAA | 2 | 10 | 60 | 15 | 12 | 91 | Bu$^t$ | Bu$^t$ | 20 |

4. The process, according to claim 1, wherein the reaction temperature is in the range of 0° C.–25° C.

5. The process, according to claim 1, wherein the content of water in the reaction mixture is in the range of 15% to 25% v/v.

6. The process, according to claim 1, wherein the molar ratio between the L-threonine ester and the des-B30-insulin is above 5:1.

7. The process, according to claim 1, wherein the water miscible organic solvent is selected from the group consisting of methanol, ethanol, 2-propanol, 1,2-ethandiol, acetone, dioxane, tetrahydrofuran, formamide, N,N-dimethylformamide, N,N-dimethylacetamide, N-methylpyrrolidone, hexamethylphosphortriamide, acetonitrile and DMSO.

8. The process of claim 1 wherein the solvent is selected from the group consisting of formamide, N,N-dimethylformamide, N,N-dimethylacetamide, N-methylpyrrolidone, hexamethylphosphortriamide, acetonitrile and DMSO.

9. The process, according to claim 1, comprising including acid in the reaction mixture to between 0.5 and 5 equivalents thereof per equivalent of L-threonine ester.

10. The process, according to claim 9, wherein the acid is an organic acid, selected from the group consisting of formic acid, acetic acid, propionic acid and butyric acid.

11. The process, according to claim 1, wherein the weight ratio between trypsin and des-B30-insulin in the reaction mixture is between 1:200 and 1:1.

12. The process according to claim 1 including amidation with yields exceeding 95%.

* * * * *